United States Patent [19]

Edelman et al.

[11] Patent Number: 4,818,684

[45] Date of Patent: Apr. 4, 1989

[54] AUTO-ANTI-IDIOTYPIC MONOCLONAL ANTIBODIES TO STEROID RECEPTORS AND USES THEREOF

[75] Inventors: Isidore S. Edelman, New York; Bernard F. Erlanger, Whitestone; Eftihia Tzilianos, Astoria; William L. Cleveland, New York, all of N.Y.

[73] Assignee: The Trustees of Columbia University in the City of New York, New York, N.Y.

[21] Appl. No.: 774,289

[22] Filed: Sep. 10, 1985

[51] Int. Cl.$^4$ .................. G01N 33/531; G01N 33/577; C01N 15/00

[52] U.S. Cl. .......................................... 435/7; 424/3; 435/68; 435/172.2; 435/240.26; 435/240.27; 435/948; 436/548; 436/817; 436/823; 530/387; 530/413; 530/808; 935/89; 935/95; 935/106; 935/110

[58] Field of Search .................. 436/65, 510, 518, 536, 436/548, 808, 809, 814, 817; 435/7, 68, 172.2, 240, 241, 272, 810, 240.26, 240.27, 948; 935/89, 95, 106, 110; 530/387, 388, 808, 413

[56] References Cited

U.S. PATENT DOCUMENTS 4,536,479 8/1985 Vander-Mallie .................. 435/25 X

OTHER PUBLICATIONS

Wasserman, et al., Proc. Natl. Acad. Sci., U.S.A., vol. 70, pp. 4810–4814, Aug. 1982.
Venter et al., Federation Proceedings, vol. 43, No. 10, Jul. 1984.
Erlanger et al., Monoclonal and Anti-Idiotype Antibodies: Probes for Receptor Structure and Function, Alan R. Liss, Inc., New York, pp. 163–176, 1984.
Kahler et al, Nature, vol. 256, Aug. 1975, pp. 495–497.

Primary Examiner—Sidney Marantz
Attorney, Agent, or Firm—John P. White

[57] ABSTRACT

A competitive immunoassay for a steroid receptor has been developed in which monoclonal antibodies capable of binding to the steroid receptor are competitively bound by anti-steroid antibodies capable of binding to the steroid. The presence or amount of monoclonal antibody-anti-steroid antibody complex formed is related to the amount of steroid receptor present in the assayed material.

A histochemical assay is also provided for detecting the amount of a steroid-receptor complex in a biological sample. This assay involves (1) adding an amount of steroid to the sample to form a steroid-receptor complex; (2) contacting the complex with a monoclonal antibody capable of binding to the complex; (3) removing any unbound monoclonal antibody; (4) adding a detectably labeled antibody capable of binding to the monoclonal antibody; (5) determining the amount of labeled antibody bound to the monoclonal antibody; and (6) determining the amount of steroid-receptor complex.

The invention further provides a method of purifying receptors to a steroid hormone using monoclonal antibodies capable of binding to the receptor, and a method for producing a monoclonal anti-idiotypic antibody capable of binding to a steroid receptor.

17 Claims, 11 Drawing Sheets

AUTO-ANTI-IDIOTYPIC MONOCLONAL ANTIBODIES TO STEROID RECEPTORS AND USES THEREOF

The invention described herein was made with Government support under grant numbers NS-15581 and AM 25536 from the National Institutes of Health, U.S. Department of Health and Human Services. The Government has certain rights in the invention.

BACKGROUND OF THE INVENTION

Within this application several publications are referenced by arabic numerals within parentheses. Full citations for these references may be found at the end of the specification immediately preceding the claims. The disclosures of these publications in their entireties are hereby incorporated by reference into this application in order to more fully describe the state of the art to which this invention pertains.

Radiolabeled steroids have been used to identify and characterize the structure and function of receptors such as the glucocorticoid receptor. However, attention has now been focused on the use of antibodies as probes, not only for the above purposes but also as a means to purify the receptor by immunoadsorbent techniques. Highly purified, but non-homogeneous preparations of receptor have been used to raise both polyclonal (1-5) and monoclonal (6-9) antibodies to the glucocorticoid receptor. Because of the unstable nature of the glucocorticoid receptor in the absence of ligand, the receptor in such preparations has been isolated with bound ligand. The ligand would thus mask the antigenic determinants at the ligand combining site and this may be one of the reasons, that apart from the monoclonal antibody GR-45, which has been shown to inhibit steroid binding to the unoccupied receptor (7), all other antibodies thus raised were directed at epitomes other than those located at the combining site of the glucocorticoid receptor.

This invention concerns a new method to prepare anti-receptor antibodies that does not require previous purification of the receptor. It employs an anti-idiotypic route, that has been previously used to obtain both poly and monoclonal antibodies to other receptors (10-19) and is based on the one step methodology described by Cleveland et al. (11) for obtaining monoclonal antibodies to the combining site of the acetylcholine receptor. One embodiment of this invention utilizes a triamcinolone derivative, i.e. a hapten, to obtain anti-idiotypic antibodies directed at epitopes in the vicinity or the combining site of the glucocorticoid receptor.

The monoclonal anti-idiotypic antibodies of this invention preferably mimic receptors or ligands of receptors. We define a receptor as a molecular structure that interacts with another structure, referred to as a ligand, as part of a biological process. Receptors can include, but are not restricted to, enzymes, immunoglobulins, lymphokines, cell surface molecules, attachment sites on viruses and cells, specific binding proteins such as those which bind nucleic acids, hormone binding molecules and metal-binding molecules such as calmodulin. A ligand is similarly defined as a structure that reacts with a receptor as defined above. In addition to binding to a receptor, a ligand as defined herein may act as an agonist or as an antagonist with respect to the receptor.

Antibodies arise when an animal is immunized with a particular antigen. The variable regions of such antibodies contain the antigenic determinants known as the idiotype which is usually associated with antigen specificity. Anti-idiotypic antibodies may arise when an animal is injected with specific idiotypic antibody molecules which have been previously obtained and purified. In such an experiment the animal immunized with the idiotypic antibody produces antibodies directed against the idiotypic determinants of the injected antibody. The idiotypic antibodies may then bind to either the antigen or the anti-idiotypic antibodies so produced. Regardless of functional differences, macromolecules having the same binding specificities can also show homologies at their binding sites. Thus immunizing an animal with purified idiotypic antibodies raised against an antigen which is a ligand for a biological receptor may raise anti-idiotypic antibodies which bind to either the idiotypic antibodies or to the receptor for the ligand (10).

Anti-idiotype antibodies thus afford one route to functional anti-receptor antibodies.

Previous methods for the production and study of anti-receptor antibodies required immunizing animals with purified receptors in order to raise the desired antibodies (31,32,33).

Recently (10), a procedure was described for preparing antibodies to the acetylcholine receptor (AChR) based on immunoglobulin idiotypes and on the abovementioned hypothesis that, regardless of functional differences, macromolecules of the same specificity will show structural homologies in their binding sites. Antibodies were prepared in rabbits to a structurally constrained agonist of AChR, trans-3,3'-bis(α-trimethylammonium)azotoluene bromide (BisQ) (34,35). These antibodies mimicked the binding specificity of AChR in its activated state (36) i.e., agonists were bound with affinities that were in accord with their biological activities whole antagonists were bound poorly. Rabbits were then immunized with a specifically purified preparation of anti-BisQ antibodies to elicit a population of anti-idiotypic antibodies specific for the binding sites of anti-BisQ. A portion of the anti-idiotypic antibodies (27,28) produced in the second set of rabbits cross-reacted with determinants on AChR preparation from *Torpedo californica, Electrophorus electricus* and rat muscle. Moreover, several of the rabbits showed signs of experimental myasthenia gravis, in which circulating AChR antibodies ar typically found. Anti-idiotypic antibodies against the thyrotropin receptor have also been reported (16). In that experiment, thyrotropin (TSH) specific antibodies (idiotypic) raised in rats were injected into rabbits which then produced the anti-idiotypic antibodies against the rat anti-TSH antibodies.

It has been postulated that the anti-idiotypic response plays a role in regulating the immune response (27,28,16). According to this theory, injection of an antigen elicits, in addition to antibodies to the antigen, other populations that include anti-idiotypic antibodies directed at the combining sites of the antigen-specific antibodies. If the antigen-specific antibodies recognize a ligand of a receptor, then the anti-idiotypic antibodies should bind receptor.

In the past, the spontaneous generation of anti-idiotypes in response to immunization against an antigen has seldom been detected (30). Recently however, the spontaneous appearance of auto-anti-idiotypic antibody was observed during a normal human immune response to tetanus toxoid (37). Similarly, immunization with insulin was observed to cause the spontaneous appearance of insulin receptor-specific antibodies (30).

The difficulty in detecting the anti-idiotypic response results from the low titres of circulating anti-idiotypic antibodies formed (10,30) and to the observation that the cellular events giving rise to the anti-idiotypic response are only a transient phenomenon. Attempts to utilize the auto-anti-idiotypic response to produce anti-idiotypic antibodies would also involve technical problems that arise from the formation of immune complexes, an important limitation of serological studies.

The present invention surprisingly overcomes the aforementioned limitations by providing a method for producing anti-idiotype antibodies which depends on the use of hybridoma technology to immortalize the cells which produce the anti-idiotype antibodies. By immortalizing and cloning the cells active at the time of cell harvest, the cellular events are "frozen" in time, making it possible to produce and study clones and large quantities of their products that may have only a transient existence in vivo. Moreover, since the immortalized clones are separated from each other, this approach avoids the technical problems that arise from the formation of immune complexes. It should be understood that the method for this invention eliminates the need to obtain a purified idiotypic antibody in order to produce the anti-idiotypic antibody and the need to obtain a purified receptor in order to produce the anti-receptor antibody.

In view of the low efficiency usually observed for cell fusion (about one antibody-producing cell in one thousand is immortalized), combined with the low titres of naturally occurring anti-idiotypic antibodies and the possibility that the low titres may well have resulted from suppression of the very cells that produce such antibodies, it should further be understood that the success of this auto-anti-idiotypic method is indeed an unexpected and surprising result. The antibodies so obtained are useful in immunoassays to quantify receptors in tumors, e.g. of the breast, prostate and lymphoid tissues; in immunohistochemical assays to localize receptors; in immunoabsorption methods to obtain purified receptors and in drug screening methods to identify drugs which bind to a receptor or ligand.

SUMMARY OF THE INVENTION

A competitive immunoassay for a steroid receptor is provided which comprises contacting material suspected of containing the steroid receptor with (1) anti-steroid antibodies or fragments thereof capable of binding to the steroid and (2) monoclonal antibodies capable of binding to the steroid receptor and the anti-steroid antibodies or fragments thereof. Under suitable conditions the monoclonal antibodies bind to the steroid receptor. Those monoclonal antibodies not bound to the steroid receptor bind to the anti-steroid antibodies or fragments thereof, forming a complex. The presence or amount of the complex so formed is determined and related to the presence, concentration or activity of the steroid receptor in the assayed material.

Also provided is a histochemical assay for detecting the presence or amount of a steroid-receptor complex in a biological sample. This assay comprises incubating the biological sample with an appropriate amount of the steroid under suitable conditions permitting the steroid to bind to the receptor, forming a steroid-receptor complex. The incubated sample is then contacted with a monoclonal antibody capable of binding to the steroid-receptor complex under suitable conditions permitting the monoclonal antibody to bind to the steroid-receptor complex. Any unbound monoclonal antibody is removed from the sample, and the sample is contacted with a detectably labeled antibody or fragment thereof capable of binding to the monoclonal antibody. By determining the presence of the detectably labeled antibody bound to the monoclonal antibody, the presence or amount of the steroid-receptor complex may be determined.

The invention also concerns a method for obtaining purified receptors to a steroid hormone. This method involves immobilizing, on a solid support, a monoclonal antibody to a receptor and contacting it with material containing receptors to the steroid hormone under suitable conditions permitting the monoclonal antibody to bind to the receptors. Any unbound material is removed from the immobilized monoclonal antibodies and the bound receptors are eluted from the monoclonal antibodies with a suitable eluent to yield purified receptors.

A method for producing a monoclonal anti-idiotypic antibody capable of binding to a steroid receptor is further provided. This method comprises contacting lymphoid cells of an animal with an effective antibody-raising amount of an appropriate antigen. At a suitable time the lymphoid cells are collected and fused with appropriate myeloma cells to produce a series of hybridoma cells, each of which produces a monoclonal antibody. The series of hybridoma cells are screened to identify a monoclonal antibody capable of binding to the steroid receptor, and a cell so identified is separately cultured in an appropriate medium. The monoclonal anti-idiotypic antibody produced by the hybridoma cell is then separately recovered.

Controls with no inhibitor were included. Add 25λ of 50% (NH$_4$)$_2$SO$_4$ precipitated 8G11-C6 (1.045 micrograms mix and incubated for 2 hours at 37° C. Blanks with only PBS were included as well. The inhibitors used in FIG. 7 were triamcinolone acetonide (■), rabbit serum albumin (●) and triamcinolone -RSA ( ▲). The inhibitors used in FIG. 8 were estradiol-17β-RSA (●), testosterone RSA (○), triamcinolone-RSA ( ■ ), deoxycorticosterone RSA (▲) and cortisone-RSA (Δ)

Figure 9:
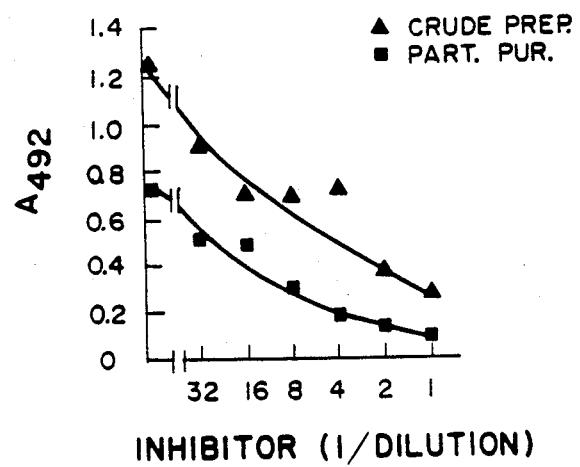

FIG. 9. Inhibition of binding of 8G11-C6 to anti-steroid Fab fragments with rat liver cytosol (▲) or partially purified glucocorticoid receptor (■). The method used was similar to that described in the exerimental procedure. The only difference being that, to 200λ of rat liver cytosol or partially purified glucocorticoid receptor preparations, that were diluted 2fold serially in PBS, 1.045 micrograms of 50% (NH$_4$)$_2$SO$_4$. precipitated 8G11 C6 was added and preincubated at room temperature for 15 mins. 200λ of the incubation mixture was then added to microtiter wells previously coated with 10 ng anti-steroid Fab fragments and incubated for 2 hrs at 37° C.

Figure 10:
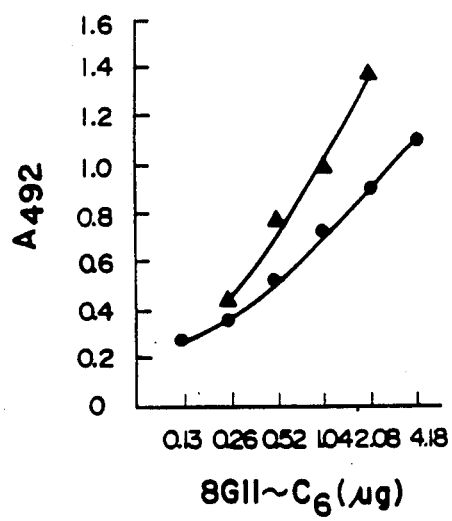

FIG. 10. Binding of 8G11-C6 to partially purified glucocorticoid receptor. 100 microliters containing either 1.08 micrograms (▲) or 0.54 micrograms (●) of a partially purified receptor preparation in 0.1M NaHCO$_3$ were added to the wells of the polystyrene plastic and incubated overnight at 4° C. The wells were washed 2× with PBS tweens and various amounts of a 2-fold serially diluted 50% (NH$_4$)$_2$SO$_4$ precipitated preparation of 8G11-C6 added. See methods section for the methodology employed.

Figure 11:
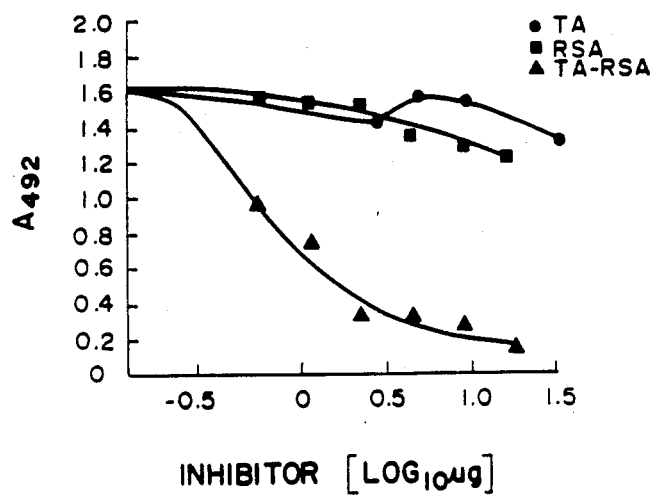

FIG. 11. Inhibition of binding of 8G11-C6 to partially purified glucocorticoid receptor. 200 microliters containing 0.54 micrograms protein of a partially purified receptor preparation in 0.1M NaHC03 pH 9.3 was added to the wells of polystyrene plates. These were incubated for 2 hrs at 37° C. Washed 2×with PBS coniters of inhibitor taining 0.02% tween. Add 175 microl serially diluted 2-fold and preincubate for 20 min at room temperature before adding 0.836 micrograms of 50% (NH$_4$)$_2$SO$_4$ ppt 8G11-C6, mixing and incubating for 2 hrs 37° C. See methods for the methodology employed. The inhibitors used were triamcinolone acetonide (●), rabbit serum albumin ( ■ ), and triamcinolone - RSA (▲).

DETAILED DESCRIPTION OF THE INVENTION

As previously mentioned, this invention involves the use of anti-idiotypic antibodies, preferably monoclonal, to detect and quantify receptors, e.g. receptors to steroids such as estrogen, androgen and glucocorticoid receptors in appropriate tumors. Methods for obtaining the necessary anti-receptor antibodies are discussed in detail below. "Antibody" as the term is used herein encompasses intact antibody and suitable fragments thereof, e.g. Fab fragments which are also capable of binding to the respective antigen.

One embodiment making use of such antibodies is an immunoassay based on the competitive inhibition of binding of idiotypic antibodies such as anti-ligand, e.g. anti-steroid, antibodies to anti-idiotypic antigen. bodies, the binding inhibition being caused by the presence of receptors that are also capable of binding to the anti-idiotypic antibodies. The method involves contacting material suspected of containing the steroid receptor with (i) anti-steroid antibodies or fragments thereof capable of binding to the steroid and (ii) monoclonal antibodies which are capable of binding to the steroid receptor and of binding to the anti-steroid antibodies or fragments thereof. The contacting is conducted under suitable conditions permitting the monoclonal antibodies to bind to the steroid receptor and permitting the monoclonal antibodies not bound to the steroid receptor to bind to the anti-steroid antibodies or fragments thereof to form a complex. The presence or amount of the complex so formed is then determined and related to the presence, concentration or activity of the steroid receptor in the assayed material.

Conventional ELISA techniques which are known in the art may be used to carry out the above-described method. Thus the anti-steroid antibodies or suitable fragments thereof, e.g. Fab fragments, may be immobilized on a suitable support such as microtiter plate by conventional methods. Microtiter plates coated with an idiotypic antibody, e.g. the anti-steroid antibody (or fragment thereof) bind to corresponding anti-idiotypic antibodies quantitatively. After contacting a sample, e.g. a high speed supernatant or cytosol fraction of a tissue extract, with the ant-ligand, e.g. anti-steroid, antibodies and the monoclonal anti-idiotypic antibodies under suitable binding conditions, material not bound to the immobilized anti-ligand, e.g. anti-steroid, antibodies are removed from the immobilized antibodies, i.e. are washed from the plate. The presence or amount of complex formed between the immobilized anti-ligand, e.g. anti-steroid antibodies and the monoclonal anti-idiotypic antibodies is then determined.

The presence or amount of the complex formed may be determined by conventional methods known in the art. For example, the complex may be contacted with a detectably labeled antibody capable of binding to the monoclonal antibody under suitable conditions permitting the labeled antibody to bind to the monoclonal antibody of the complex. Thus where the monoclonal antibody is of murine origins, radiolabeled, enzymelabeled, chemiluminescent, fluorescent, etc. anti-mouse antibody may be used to bind to the monoclonal antibody of the complex. The presence or amount of labeled antibody bound to the complex is then determined and related to the presence or amount of the complex. As will be apparent to those skilled in the art the relationship between the amount of the complex so detected and the amount of receptor in the sample is an inverse relation. Thus, the greater the amount of complex detected, the less receptor is present in the sample. By this method receptors to estrogen, androgen or glucocorticoid steroids, for example, may be assayed.

Another embodiment of this invention involves an immunohistochemical assay for the presence or amount of a steroid-receptor complex in a biological sample. Tumors that contain significant concentrations of receptors may or may not be regulaed (in growth and metabolic activity) by the appropriate steroid depending on whether the receptors are biologically active. One index of biological activity (or the potential for activity) s binding of the steroid-receptor complex the genome of target cells. Since certain anti-idiotypes bind to steroid-receptor complexes, the appropriate anti-idiotype should reveal nuclear accumulation of steroid-receptor complexes.

The histochemical assay for the presence or amount of a steroid-receptor complex in a biological sample involves first incubating the biological sample, e.g. tissue slices, with an appropriate amount of the steroid under suitable under suitable conditions permitting the steroid to bind to the receptor to form the steroid-receptor complex.

The incubated sample is then contacted with a monoclonal antibody capable of binding to the steroid-receptor complex, e.g. an appropriate monoclonal antiidiotypic antibody, under suitable conditions permitting the monoclonal antibody to bind to the steroid-receptor complex.

Any unbound monoclonal antibody remaining is then removed from the sample. The sample is then contacted with a detectably labeled antibody or fragment thereof capable of binding to the monoclonal antibody. The presence or amount of the detectably labeled antibody or fragment thereof bound to the monoclonal antibody is then determined and thereby the presence or amount of the steroid-receptor complex in the sample is als detected.

This method is particularly useful for assaying for receptor-steroid complexes containing estrogen, androgen or glucocorticoid steroids, for example, and the respective appropriate receptor. The method may also be used to study and possibly diagnose or monitor mamiate steroid is mary carcinoma, in which case an appropr estradiol-17$\beta$, prostatic carcinoma, in which case an appropriate steroid is dihydrotestosterone, or lymphomas, in which case an appropriate steroid is triamcinolone.

In conducting the above-described histochemical assay, detection of the monoclonal anti-idiotypic antibody bound to the steroid-receptor complex may be conveniently effected by conventional methods involving a detectably labeled second antibody, as previously described for the competitive binding assay above. For example a murine-derived monoclonal antibody bound to the steroid-receptor complex may be counter-stained with peroxidase labeled goat anti-mouse antibodies. The peroxidase reaction over nuclei will reveal the presence of receptors at the putative active site. Fluorescein-labeled goat anti-mouse antibodies can also be used. In that case, receptors in nuclei will be revealed by the appearance of fluorescence.

This invention also involves a method for obtaining purified receptors to a ligand such as a steroid hormone. The method involves first immobilizing a monoclonal antibody to the receptor on a suitable support, e.g. cyanogen bromide-activated Sepharose. Methods for obtaining and purifying such monoclonal antibodies are provided hereinafter.

The immobilized monoclonal antibody is then contacted with material containing receptors to the ligand, e.g. steroid hormone, under suitable conditions permitting the monoclonal anti-idotypic antibody to bind to the receptors. Unbound material including extraneous protein is removed from the immobilized monoclonal antibodies, e.g. by washing with a suitable buffer. The bound receptors are then eluted from the immobilized monoclonal antibodies with a suitable eluent to yield the purified receptors. A suitable eluent for the receptor being obtained includes compounds which inhibit the binding of the monoclonal antibody to the By way of example, $\xi$-triamcinolone-glycyllysylglycine may be used to elute glucocorticoid receptors from monoclonal antibody 8G11-C6 which binds to such receptors and is described in detail hereinafter.

Purified receptors obtained by the method described above may be stored at $-70°$ C. in a suitable medium such as PBS-buffered 2 mM thioglycerol. The purified receptors may be used in competitive binding assays to screen drugs for ligand-like activity, e.g. glucocortiscre coid activity. Such an assay may measure displacement of binding of labeled ligand or analog thereof to the purified receptor, for example of radiolabeled triamcinolone acetonide to the purified glucocorticoid receptor.

This invention also concerns a method for producing a monoclonal anti-idiotypic antibody capable of binding to a receptor, e.g. a steroid. The method comprises contacting lymphoid, e.g. spleen, cells of an animal, e.g. a mouse, rat, or other vertebrate under suitable conditions with an effective antibody-raising amount of an appropriate antigen. Such contacting may be effected by growing the lymphoid cells in vitro in the presence of the antigen and collecting the cells at least about three days after the contacting.

Alternatively the contacting may be effected by injecting the antigen into the animal, e.g. by injecting the with a solution peating the injection after about two to about four weeks. The lymphoid cells are then collected at a suitable time, e.g. at least about 3 days after the contacting and fused with appropriate myeloma cells by conventional methods to produce a series of hybridoma cells, each of which produces a monoclonal antibody. The series of hybridoma cells so produced is then screened under suitable conditions to identify those which secrete a monoclonal antibody capable of binding to the recetor e.g. steroid receptor. Screening may be effected by immunoassay of the hybridoma culture medium against an immobilized antibody to the antigen and a labeled antibody capable both of binding to the monoclonal anti-idiotypic antibody under appropriate conditions and of being detected. Alternatively, the hybridoma cells are screened by immunoassay of the hybridoma culture medium against immobilized receptor and a labeled antibody capable both of binding to the monoclonal anti-idiotypic antibody under appropriate conditions and of being detected.

A hybridoma cell so identified is then separately cultured in an appropriate medium and the monoclonal antiidiotypic antibody produced by the hybridoma cell recovered under suitable conditions known in the art.

In the practice of this method, the antigen may comprise a hapten capable of binding to the steroid receptor, the hapten being conjugated to a suitable protein, e.g. bovine or rabbit serum albumin, keyhole limpet hemocyanin or thyroglobulin. By this method monoclonal antibodies may be produced which are capable of binding to receptors an estrogen, e.g. estradiol-17, β, androgen, e.g. dihydrotestosterone or glucocorticoid steroid, e.g. triamcinolone.

Monoclonal anti-idiotypic antibodies capable of binding to a steroid receptor under suitable conditions may thus be produced, including a monoclonal anti-idiotypic antibody capable of binding to an estrogen receptor, an androgen receptor or glucocorticoid receptor.

By way of example, a hybridoma cell line was obtained using the above-described auto-anti-idiotypic method (see also reference 3) which secretes a monoclonal antibody, 8G11-C6, specific for rat liver glucocorticoid receptor. The cell line has been deposited with the American Type Culture Collection, Rockville, Md. and assigned number ATCC HB 8708.

According to the anti-idiotypic (27,28) network theory of Jerne (29), the variable regions of antibodies may in turn give rise to a secondary set of anti-idiotypic Hence, if the ligand of a receptor is used as a hapten, some of the idiotypic antibodies will have binding specificities that resemble the receptor. The anti-idiotypes of this idiotypic subset of antibodies should mimic the ligand of the receptor and be directed at epitopes close to or near the ligand combining site of the receptor.

The strategy employed was to use the hapten triamcinolone, a ligand of the glucocorticoid receptor, to raise polyclonal antibodies in rabbits and monoclonal antibodies in mice. In the rabbits only polyclonal idiotypic anti-steroid antibodies were isolated by affinity chromatography. These were used in screen by ELISA for anti-idiotypic antibody formation in mice using a goat anti-mouse peroxidase label. However, as this is a polyclonal system only, some and not all of the idiotypic antibody subsets present will mimic the glucocorticoid receptor. Furthermore, the receptor-like idiotypes in this population would not necessarily represent the majority. This would require more specific techniques than those used in the present study to elute the anti-steroid from the affinity column. Attempts to elute anti-steroid with the ligand triamcinolone proved fruitless. For this reason, specific anti-idiotypes that would bind to the glucocorticoid receptor were selected for, by immobilizing anti-idiotypic antibodies to CNBr-Sepharose anti-mouse beads and testing their ability to remove high affinity [$^3$H]TA binding from rat liver cytosol. This strategy resembles that used to isolate anti-idiotypic antibodies to the acetylcholine receptor (11). The major difference between the two being that purified acetylcholine receptor was used to screen for anti-idiotypic acetycholine activity in the former study whereas in the present study anti-idiotypic glucocorticoid receptor activity was determined with crude rat liver cytosol preparations by a depletion assay and verified with characterization studies. This demonstrated that purified receptor preparations were not necessary either for immunizing or screening. Other anti-idiotypic antibodies that are cross reactive with insulin receptor (12), chemotactic receptors of the neutrophil (15), β-adrenergic receptor (13,14). Previous receptor (17) dopamine receptor (18), TSH receptor (16) have also been raised by using ligand and/or idiotypic antibodies as antigens.

In order to induce antibodies, with ligand-like properties the first requirement was to make a hapten that could interact with the glucocorticoid receptor. For this reason, triamcinolone was derivatized to triamcinolone δ-ketohexanoic hydroxysuccinimide ester at the 16 and 17 position of the D ring of the steroid, as this modification would affect its binding activity to the receptor the least. The triamcinolone protein conjugates that were synthesized interacted with the glucocorticoid receptor and elicited both idiotypic and anti-idiotypic antibodies. The polyclonal idiotypes raised by the triamcinolone BSA conjugate in rabbits had high affinities for triamcinolone acetonide and steroid binding resembled those of the glucocorticoid receptor. The anti-idiotypes, and in particular 8G11-C6, obtained from mouse hybridomas, that were raised by immunizing with triamcinolone thyroglobulin, bound the idiotypes specifically. The binding of 8G11-C6 roid was inhibited by triamcinolone-RSA conjugates indicating that this interaction occurred at the combining site of the idiotype. It also showed that the 8G11-C6 cross-reacted with the glucocorticoid receptor in crude rat liver cytosol preparations and did not bind to the anti-steroid in the inhibitor studies. This was confirmed by the findings that partially purified glucocorticoid receptor preparations also inhibited the anti-steroid idiotype from reacting with the anti-idiotypic 8G11-C6. Furthermore, the cross reaction of 8G11-C6 with partially purified glucocorticoid receptor preparation was inhibited by triamcinolone-RSA conjugates. Also, the patterns of inhibition of binding of 8G11-C6 to the anti-steroid and of 8G11-C6 to the glucocorticoid receptor by different steroid-RSA conjugates were similar. These ELISA results established the interrelationship of hapten-idiotype, anti-idiotype and glucocorticoid receptor.

The anti-idiotype 8G11-C6 was initially raised to idiotypic typic antibodies that were specific for triamcinolone. However, the results show the binding of 8G11-C6 to the anti-steroid is inhibited by steroid-RSA conjugates rather than by triamcinolone acetonide. As the ligand is a low M.W., organic molecule it will only occupy a small portion of the total combined surface area of the anti-steroid. Hence 8G11-C6 will be able to cross-react with the anti-steroid even though triamcinolone is present. On the other hand, in the case of the steroid-RSA conjugate almost the total area will be occupied and the binding of 8G11-C6 to the anti-steroid will be inhibited. This is supported indirectly by the finding that the patterns of steroid-RSA conjugate inhibition of 8G11-C6 reacting with anti-steroid by ELISA was similar to that obtained with steroid inhibition RIA studies with the anti-steroid. As similar ELISA results were obtained when the glucocorticoid receptor replaced the anti-steroid, it was assumed that the same phencmenon occurred in this case as well. This was verified by the ability of 8G11-C6 immobilized on CNBr-Sepharose anti-mouse beads to deplete either free or [$^3$H]TA labeled receptor from rat liver cytosol. This again indicates that triamcinolone is not able to block the binding of 8G11-C6 to the receptor. Further evidence of interaction 8G11-C6 with [$^3$H]TA glucocorticoid receptor was obtained from the sucrose density studies.

The RSA inhibition studies demonstrate that 8G11 C6 is specific for the glucocorticoid receptor rather than other steroid receptors such as estrogen. This shows that the specificity of the receptor isolated is dependent on the ligand used for immunization and can be used in place of purified glucocorticoid receptor to isolate monoclonal antibodies. These results also show that 8G11-C6 could be used as an immunochemical to prepare an affinity column to purify the glucocorticoid receptor. Such an affinity column will have one advantage of being specific for the glucocorticoid receptor and not other steroid binding proteins. As the binding of triamcinolone does not affect the binding of 8G11-C6 to the receptor, the glucocorticoid receptor can be radiolabeled with [$^3$H]TA and its binding and elution profiles monitored. Furthermore, as the sucrose density studies demonstrate that 8G11 C6 has a low affinity for the glucocorticoid receptor, it will enable the receptor to be eluted readily from the affinity column thus increasing the yield of undenatured receptor. In fact, the steroid-RSA conjugate could be used to elute the receptor from such a column. 8G11-C6 together with other anti-idiotypic antibodies that cross-react with the glucocorticoid receptor may be used as probes instead of radiolabeled ligands to identify and characterize the structure and function of the receptor.

EXAMPLES

Materials and Methods

New Zealand white rabbits were obtained from Pocono Farms (Canadensis, Pa.) and BALB/c mice (West Senica, N.J.). Sprague Dawley rats from Charles River Laboratories (Wilmington, Ma.). Acetylbutyric acid, N-hydroxysuccinimide, dicyclohexylcarbodiimide were from the Aldrich Chemical Co. (Milwaukee, Wis.). Norit A and Celite S45 were from Fisher Scientific, silica gel 60 from Merck AG, Darmstadt. AH Sepharose 4B, Sephadex G100 and Protein A were from Pharmacia Fine Chemicals (Uppsala, Sweden). Typing serum, rabbit and anti-serum to mouse Gl(lgF) lgA, lgM, K light chain were obtained from Bionetics, Inc. (Kensington, Md.) and goat anti mouse lgG3 was obtained from Tago Inc. (Burlingame, Calif.) as were the peroxidase conjugated goat anti-mouse lgG+lgM antibodies. Iscoves' modified Dulbecco's medium (IMDM), the nutrient mixture F12 (HAM) and penicillin-streptomycin were obtained from Grand Island Biological Co. (Grand Island, N.Y.). Fetal calf serum was purchased from Sterile Systems (Logan, Utah).

The steroid derivative 17[(C4-carboxy-1-methyl-butylidine)-bis(oxy)]-9-fluoro 11 -β-21 -dihydroxypregna-1-,4-diene, was a gift from the Upjohn Co., Kalamazoo, Mich., U.S.A.

The labeled steroids [$^{1,2,43}$H]triamcinolone acetonide and 6,7[$^3$H] dexamethasone were purchased from Amersham-Buchler (Braunschweig).

EXAMPLE 1

Synthesis of the Triamcinolone (TA)-Protein Conjugate

I. δ-ketohexanoic-N-hydroxysuccinimide ester 0.024 moles 4-acetylbutyric acid was stirred in approximately 60 ml dioxane. To this stirred solution was added a solution of 0.036 moles N-hydroxysuccinimide in dioxane. More dioxane was added until all of the Nhydroxysuccinimide was in solution. Finally 0.025 moles of dicylohexylcarbodiimide in dioxane was added and the solution, in a total volume of 100 ml, stirred overnight. The insoluble dicyclohexylurea was removed by filtration and the filtrate concentrated by evaporation in a rotary evaporator. The product was extracted with 200 ml methylene chloride. After 5 washes with water to remove dioxane and unreacted N-hydroxysuccinimide, the methylene chloride extract was dried with solid magnesium sulfate and decolorized with norit A. The solids were removed by filtration through celite 545 and the filtrate was concentrated by rotary evaporation. The product was examined for the presence of the ester by TLC using an analytical silica gel TLC plate and eluting with 2% methanol in methylene chloride (v/v). The ester was identified by the Fe-hydroxamate test (19).

Purification of δ-ketohexanoic-N-hydroxysuccinimide ester

Approximately 9 g of the concentrate containing the ketohexanoicsuccinimide ester was chromatographed on a column containing 160 g Silica gel 60 in chloroform. After washing with 100 ml chloroform, the δ-ketohexanoic-hydroxysuccinimide ester was eluted with 3% methanol in chloroform (v/v). The first 250 ml were discarded after which 20 ml fractions were collected, until all the color was eluted from the column. The purity of δ-ketohexanoic-hydroxysuccinimide in the various fractions was then assessed by TLC as described above. The pure fractions were combined and evaporated to dryness.

II. Coupling of δ-ketohexanoic-hydroxysuccinimide ester to triamcionolone

Triamcinolone (0.8 g) and 0.9 g ester to triamcinolone of 6-ketohexanoic hydroxysuccinimide ester were suspended in 16 ml dioxane with stirring, followed by careful addition of 0.3 ml perchloric acid. Stirring was allowed to continue overnight at room temperature yielding a clear solution. The reaction was terminated by neutralizing with $Na_2CO_3$, and the product extracted with 100 ml methylene chloride. After washing with 200 ml $H_2O$, the upper water phase was discarded and the lower methylene chloride phase was dried over solid $MgSO_4$. After filtration and evaporation to dryness, the product was chromatographed by TLC using 10% methanol in chloroform as the developing solvent. The product was detected as an ester as before (19) and distinguished from the starting material by its strong UV activity.

Purification of triamcinolone-δ-ketohexanoic-hydroxysuccinimide ester

A chloroform solution of the product was passed through a silica gel 60 column (100 g) that had been equilibrated with chloroform. Development was with 7.5% methanol in chloroform, using a slow flow rate. Ten milliliter fractions were collected and examined for product by TLC chromatography on silica gel 60 using 10% methanol in chloroform as solvent. The fractions containing the triamcinolone-δ-ketohexanoic-hydroxysuccinimide ester were combined, concentrated by rotary evaporation and purified further by HPLC, using a ZORBOX-silica column of 21.2 mm×25cm dimensions. Methanol 3% (v/v) in chloroform at a flow rate of 16 ml/min produced 2 major peaks which were concentrated by rotary evaporation. Pure steroid ester was identified in the second peak by TLC chromatography as was described above.

III. Coupling of triamacinolone-δ-ketohexanoic hydroxysuccinimide ester to BSA, RSA or thyroglobulin A solution of $1.4 \times 10^{-4}$ moles of the steriod ester dissolved in 2 ml of tetrahydrofuran was added dropwise to a solution of $2.8 \times 10^{-6}$ moles of protein dissolved in 5 ml 0.2M Na$_2$CO$_3$/NaHCO$_3$ buffer adjusted to pH 8.0. Additional tetrahydrofuran had to be added to clarify the solution. After standing overnight at 4° C., the solution was dialyzed against several changes of distilled water. A white precipitate formed, most of which was redissolved by dropwise addition of 0.2M Na$_2$CO$_3$. Additional distilled H$_2$O was added to bring the volume to 35 ml and the suspension was centrifuged at 4° C. to remove denatured protein. The amount of steroid bound was calculated from the $E_{max}$ of the steroid ester, which was previously determined to be $1.2 \times 10^4$ at $E_{max}$243 nm. The results were 18-23 units steroid/mole RSA, 16 units steroid/mole thyroglobulin.

The other steroid conjugates namely 17$\beta$-estradiol-RSA testosterone-RSA, corisone-RSA and deoxycortisone-RSA were previously synthesized (20, 21).

EXAMPLE 2

Preparation and isolation of specifically purified polyclonal anti-steriod from rabbit serum (a) Immunization protocol New Zealand white rabbits were immunized by multiple intradermal injections of a total of 1 ml of triamcinolone-BSA (2 mg/ml) in saline emulsified with an equal volume of complete Freunds adjuvant. Booster injections were given three weeks later and then at monthly intervals. Animals were bled bi-weekly from the ear vein and the sera stored at 4° C. until required.

(b) Affinity chromatography of the anti-steroid preparation of AH-Sepharose 4B-triamcinolone column AH-Sepharose 4B (1g) 100 ml was suspended in 100 ml of 0.5N NaCl. After 15 min, the slurry was filtered on a Buchner funnel and washed with 250 ml of 0.5N NaCl and then with 250 ml water. The slurry was transferred to a centrifuge tube and washed five times with 10 ml 0.2 M NaHCO$_3$ pH 8.15. After the last wash, the supernatant was discarded and an equal volume of 0.2 M NaHCO$_3$ pH 8.15, was added followed by 58.6 mg triamcinolone N-hydroxysuccinmide ester in 3-5 ml of tetrahydrofuran. The suspension was mixed overnight at 4° C., followed by centrifugation of the gel and washing with a methanol/H$_2$O solution (1:1), distilled H$_2$O and equilibration with PBS. The gel was poured into a 10 cc Luerlock plastic syringe to obtain about a 4 ml bed volume. Storage was at 4° C.

(c) Purification of the polyclonal anti-steroid antibody

Thirty to 40 ml of serum obtained in part (a) of this example were passed slowly (±3.5 ml/hr) through the AH-Sepharose 4B triamcinolone column prepared according to (b) above. After washing with PBS to remove all unbound protein, the antibody was eluted with 0.2 M glycine pH 2.2 or 2.8. The eluate was dialyzed against 2 liters, 0.01 M PBS buffer pH 7.4 and the buffer changed at least 4 times before concentrating by vacuum dialysis at 4° C.

(d) Preparation of Fab Fragments

The method of Porter (22) was used whereby 5.5 ml of affinity purified anti-steroid antibody (20 mg) obtained in (c), above, was dialyzed against 0.1 M potassium phosphate buffer pH 7.0 containing 0.45% NaCl for 2 hrs at 4° C. To the dialysate was added 0.1 M dithiothreitol (DTT) (15 microliters) EDTA (2 mg) and 0.2 mg mercuripapain (5 microliters) and the solution was incubated overnight at 37° C. It was then dialyzed against 4 l distilled H$_2$O for 3 hrs and then against 1 liter of PBS for 2 hrs and then applied to a Sephadex G100 column (1×5×90 cms) and eluted (±5 ml/hr) with 0.01 M PBS pH 7.4. One ml fractions were collected. Fractions 53-79 were combined and examined at 280 nm for protein content. Undigested IgG and Fc fragments were removed by passage through a protein A Sepharose column (5 ml bed volume); unbound Fab was eluted with 0.01 M PBS pH 7.4. The eluate was concentrated by vacuum dialysis.

EXAMPLE 3

Preparation and isolation of monoclonal anti-idiotypic antibody

Two female Balb/c mice were immunized i.p. with 0.1 ml of a 1 mg/ml solution of triamcinolone thyroglobulin conjugate in complete Freunds adjuvant. Three weeks later the mice were boosted i.p. with the same preparation. After another 4 week interval, the animals were boosted a second time i.p. with the same preparation. Four days after the final immunization, one of the mice was splenectomized. $2 \times 10^8$ spleen cells were fused with $2 \times 10^7$ cells of a non-secreting myeloma line (P3×63-Ag 8.653) (22) according to the procedure of Kohler and Milstein (23) as modified by Sharon et al. (24). Supernatants from the hybridomas were obtained by a replica transfer technique (25) and screened for anti-idiotypic activity by ELISA. Monoclonal antibody-producing hybridomas were obtained by cloning the cells of the cultures of interest on soft agar or by using a micromanipulation technique (26). The class and subclass of the heavy chain of the monoclonal antibodies were determined by Ouchterlony and by ELISA using antimouse Ig class and subclass antisera as typing serum or to coat microtitre plates. The clones of interest were expanded by growing them in 75 cm$^2$ T-flasks. The antibodies in the culture medium were purified by precipitation in 50% saturated (NH$_4$)$_2$SO$_4$.

Enzyme-linked immunosorbent assay

The presence of anti-idiotypic antibodies in the hybridoma culture medium were assayed by a double antibody sandwich ELISA. Polystyrene microplates (Corning 25855) were coated by adding 200 microliters of 50 ng/ml affinity purified rabbit anti-steroid FAB fragments in 0.1 M NaHCO$_3$, pH 9.3, to the wells and incubating overnight at 4° C. After washing twice with 0.01 M phosphate buffer—0.14M NaCl, pH 7.4, containing 0.05% Tween-20 (PBS-Tween), the culture medium from the hybridomas was added and incubated at 37° C. for 2 hrs. The wells were washed three times with PBS-Tween and 200 microliters of 1:3,000 dilution in PBS-Tween of goat anti-mouse 1gM-1gG horseradish peroxidase (Tago) was added. After incubating 1 hr at 37°, the wells were washed three times with PBS-tween and 200 microliters substrate (7 mg o-phenylenediamine dichloride in 10 ml 0.1 M citrate-phosphate buffer, pH 4.8 containing 5 microliters of 30% H$_2$O$_2$) was added. Depending on the intensity of the color, the reaction was stopped after 5-10 min by the addition of 50 microliters 8N H$_2$SO$_4$ and the OD determined (Titretek) at 492 nm.

EXAMPLE 4

Cytosol preparation of the olucocorticoid receptor

Four to 6 days after 150-200 g Sprague-Dawley male rats were adrenalectomized, they were anesthesized with ether and the livers perfused in situ through the portal vein with 50 ml of cold saline. The livers were then removed, homogenized with a Teflon-glass homogenizer in 1.1 volume of 10 mM HEPES, containing 50 mM NaCl, 1 mM $Na_2EDTA$, 1 mM dithiothreitol (DTT) and 10% glycerol, pH 7.6, and centrifuged for 1 hr at 250,000 g at 4° C. The upper fatty layer was discarded. The supernatant was either frozen immediately in liquid-nitrogen and used for assays or labeled by incubating with 75 nM [$^3$H]triamcinolone acetonide for 2 hrs at 4° C. Unbound steroid was removed with 5% dextran-coated charcoal. The [$^3$H]TA labeled glucocorticoid receptor was partially purified by the method described by Gametchu & Harrison (9), the only modification being that the phosphocellulose was omitted from the first purification step.

EXAMPLE 5

Depletion assay using rabbit or goat antimouse Sepharose 4B to which the putative mouse anti-receptor antimouse was bound (a) Preraration of the Sepharose 4B immunoadsorbent Affinity chromatography-purified rabbit or goat antimouse IgM was coupled to cyanogen bromide activated Sepharose 4B as described by Westphal et al. (6) and in the Affinity Chromatography Handbook of Pharmacia. Cyanogen bromide (CNBr)-activated Sepharose (500 mg) was swollen in 1 mM HCl and washed on a sintered funnel with 1 mM HCl (200 ml). The gel was washed twice with coupling buffer (0.25 M NaHCO$_3$ containing 0.5 M NaCl pH 8.5) and suspended immediately in a (4 mg/3 ml) affinity purified antimouse 1 gM solution. The suspension was mixed gently by rotating either for 2 hrs at room temperature or overnight at 4° C. The mixture was then centrifuged in a clinical centrifuge and the gel sediment reacted with 1 M ethanolamine pH 8.2 either for 1 hr at room temperature or overnight at 4° C. It was then washed with 15 ml 0.1 M acetate buffer containing 1 M NaCl, pH 4.0, followed by 0.1 M borate buffer pH 8.0, and then with PBS several times and suspended in 3 volumes of PBS.

(b) Assay of supernatants for receptor binding activity

Antibody containing culture medium (1-3.5 ml) was mixed with 125 microliters of anti-mouse-Sepharose 4B beads overnight at 4° C. The anti-mouse-Sepharose 4B beads were centrifuged down and washed 3 times with 2 ml PBS. Rat liver supernatant (300 microliters) containing 0.09-0.18 pmoles of receptor was added and mixed for 2 hrs at 4° C. The gel was centrifuged down and 200 microliters of the supernatant was assayed for glucocorticoid receptor after adding 25 microliters 25 nM [$^3$H]TA and incubating it at 4° C. for 2 hrs. Unbound [$^3$H]TA was removed by adding 100 microliters 5% charcoal/dextran and allowing it to stand at 4° C. for 5 mins. Cold PBS (1 ml) was added and after 5 mins the charcoal/-dextran was centrifuged down. The supernatant was asssayed in a scintillation counter.

EXAMPLE 6

Sucrose density gradient experiments

The glucocorticoid receptor was radiolabeled by incubating 0.5 ml rat liver cytosol with 10 nM [$^3$H]TA for 2 hrs at 4° C. Five percent charcoal/dextran (0.25 ml) was added and the suspension allowed to stand for 10 min at 4° C. After centrifugation, 4° C., either 50 microliters of [$^3$H]TA radiolabeled cytosol (0.16 p moles) was incubated together with 190 microliters of PBS at 4° C., or 50 microliters of [$^3$H]TA radiolabeled cytosol together with 190 1μg 50% $(NH_4)_2SO_4$ precipitated 8GllCC6 (9 4 mg/ml).

The incubation mixture (240 microliters) was layered on 4.4 ml of a continuous 5-20% sucrose density gradient containing 10 mM Tris Hel buffer, 1 mM EDTA and 0.4 M KCl. The gradient was prepared on a 0.2 ml 40% sucrose cushion. Centrifugation was in a Beckman SW55 rotor at 300,000 g for 3 hrs. Two to 3 drop fractions were obtained by puncturing the bottom of the tube.

RESULTS

Characterization of triamcinolone BSA conjugate

Figure 1:
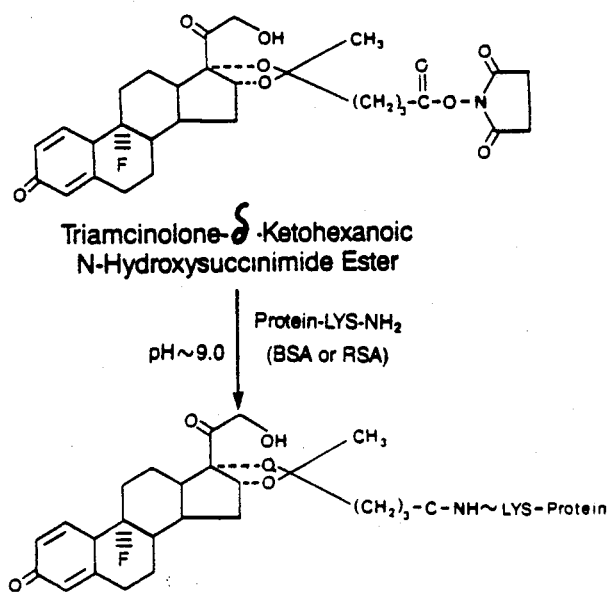
FIG. 1. Schematic representation for the preparation of the triamcinolone protein conjugate.
Figure 2:
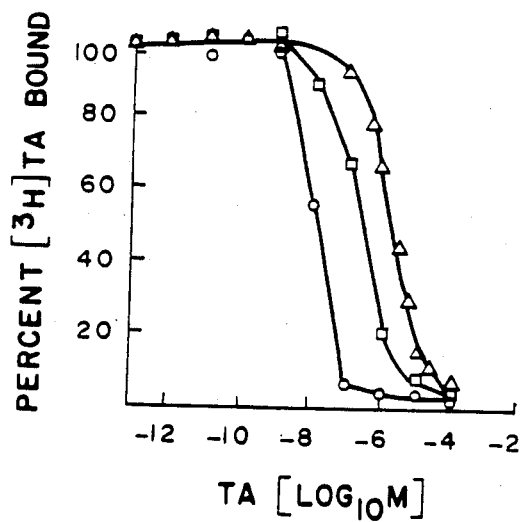
FIG. 2. Competitive inhibition of binding of [$^3$H]TA to the rat liver cytosol by increasing levels of unlabeled triamcinolone acetonide (○), steroid derivative 17-[C4-carboxy-1-methylbutylidine)bis(oxy)]-9-fluoro-11$\beta$-21-dihydroxypregna-1,4-diene, (□) and by the steroid BSA conjugate (△). Incubate in a total volume of 500 microliters, for 2 hrs at 4° C. 20 mM HEPES buffer containing 50 mM NaCl, 1 mM EDTA, 10% glycerol 0.1 mM DTT pH 7.6, 10nM [3H]TA and 200 microliters rat liver cytosol. Add 250 microliters 5% charcoal/dextran solution and after 10 min centrifuge and determine the radioactivity in 200 $\lambda$aliquot.

The triamcinolone BSA conjugate competes with [$^3$H]TA for the receptor. Its apparent Kd at 10 nM [$^3$H]TA for 3 the glucocorticoid receptor was found to be $2.5 \times 10^{-6}$ M. This is 100-fold greater than that of the ligand, triamcinolone acetonide which was found to be $1.5 \times 10^{-8}$ M under the same assay conditions (FIG. 2). The triamcinolone-BSA conjugate was also found to be immunogenic and to induce polyclonal antibodies specific for triamcinolone. Significant titers could be detected in rabbit serum immediately after the second booster injection. These were detected by precipitin tube assay by incubating rabbit serum with various concentrations ranging from 0.1-1.0 mg/ml of either triamcinolone-RSA or RSA. Precipitation was only obtained in the presence of triamcinolone-RSA and not with RSA. When pre-immune serum was used as a control, no precipitation was obtained. Portions of the anti-serum were then purified by affinity chromatography on an AH-Sepharose 4B triamcinolone column. Forty ml of serum yielded 15-20 mg anti-steroid, that could also precipitate the triamcinolone-RSA complex by the precipitin tube assay as well as Ouchterlony.

B. Characterization of polyclonal idiotypic anti-steroid antibodies by RIA

Figure 3:
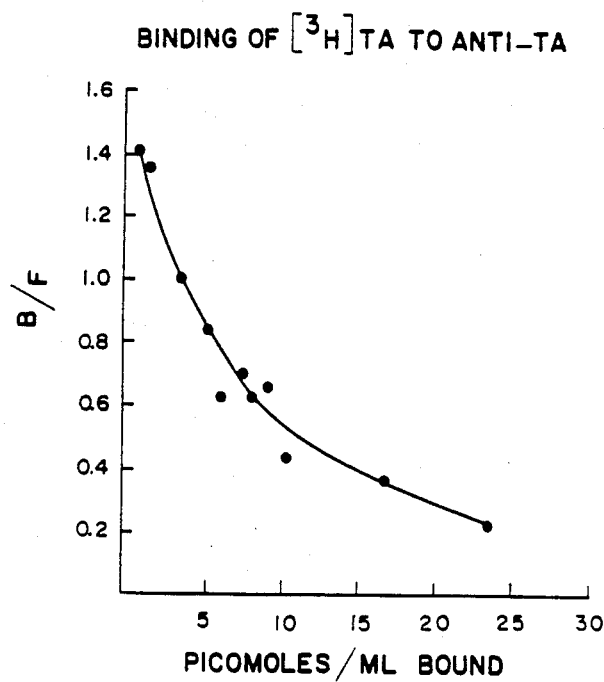
FIG. 3. Scatchard plot of the binding of [$^3$H] triamcinolone to Fab fragments of affinity purified anti-steroid antibodies. Fab fragments (0.227 micrograms) were incubated with increasing concentrations of [$^3$H] triamcinolone (0.4–62.5nM) in the presence of 0.01M phosphate buffered saline pH 7.4 containing 0.1% gelatin in a total volume of 200 microliters. Total and non-specific binding (50 micromoles triamcinolone acetonide) were determined for each of the [$^3$H] triamcinolone levels and all points were in duplicate. After incubating 1 hr at room temperature, add 1 ml cold 5% charcoal/dextran (diluted 1:40 in 0.01M PBS containing 0.1% gelatin) and let stand on ice for 10 min. Centrifuge down the charcoal/dextran, decant the supernatant into scintillation vials and determine the radioactivity.

Both the affinity purified anti-steroid antibodies as well as their Fab fragments, were found to bind [$^3$H]TA. The Kd for Fab fragments of the anti-steroid, as determined from Scatchard plots (FIG. 3), ranged from $9.3 \times 10^{-9}$M to $4.3 \times 10^{-8}$ M. The curved plot clearly indicates the heterogenous nature of the anti-steroid idiotypes. On the other hand, a linear Scatchard plot was obtained with [$^3$H]-dexamethasone and the Kd for the antisteroid Fab fragments determined to be $1.5 \times 10^{-7}$ M.

TABLE I

| Steroid | Glucocorticoid receptor [M] | Rabbit Serum 540 | | Rabbit serum 541 |
| --- | --- | --- | --- | --- |
| | | Unprocessed [M] | Affinity purified [M] | Fab fragments [M] |
| Triamcinolone | $5 \times 10^{-9}$ | $3.2 \times 10^{-9}$ | $1.5 \times 10^{-8}$ | $1.5 \times 10^{-8}$ |

TABLE I-continued

| Steroid | Glucocorticoid receptor [M] | Rabbit Serum 540 | | Rabbit serum 541 Fab fragments [M] |
| --- | --- | --- | --- | --- |
| | | Unprocessed [M] | Affinity purified [M] | |
| Dexamethasone | $7.9 \times 10^{-9}$ | $1.2 \times 10^{-7}$ | $6.2 \times 10^{-7}$ | $6.3 \times 10^{-7}$ |
| Corticosterone | $3.1 \times 10^{-8}$ | $6.3 \times 10^{-4}$ | $1.0 \times 10^{-4}$ | $1.0 \times 10^{-4}$ |
| Hydrocortisone | $1.2 \times 10^{-7}$ | $5.0 \times 10^{-6}$ | $1.0 \times 10^{-4}$ | $1.0 \times 10^{-4}$ |
| Progesterone | $2.5 \times 10^{-6}$ | $1.0 \times 10^{-4}$ | $1.0 \times 10^{-4}$ | $1.0 \times 10^{-4}$ |
| Testosterone | no inhibition | not inhibited | not inhibited | not inhibited |

Table I: Competitive inhibition of binding of [$^3$H] triamcinolone to the glucocorticoid receptor, unprocessed rabbit serum 540, affinity purified anti-steroid and anti-steroid Fab fragments. Assays with the glucocorticoid receptor included 100 ml of rat liver cytosol. $10^{-8}$ M [$^3$H]TA and increasing concentrations of steroid in a total volume of 200 ml. After incubating for 2 hrs at 4° C., 100 5% charcoal/dextran was added. Let stand for 5 mins at 4° C. Make up to 1 ml with PBS and after 5 mins centrifuge down charcoal. Decant supernatant into scintillation vials. Add 10 ml hydrofluor and count.

Figure 4:
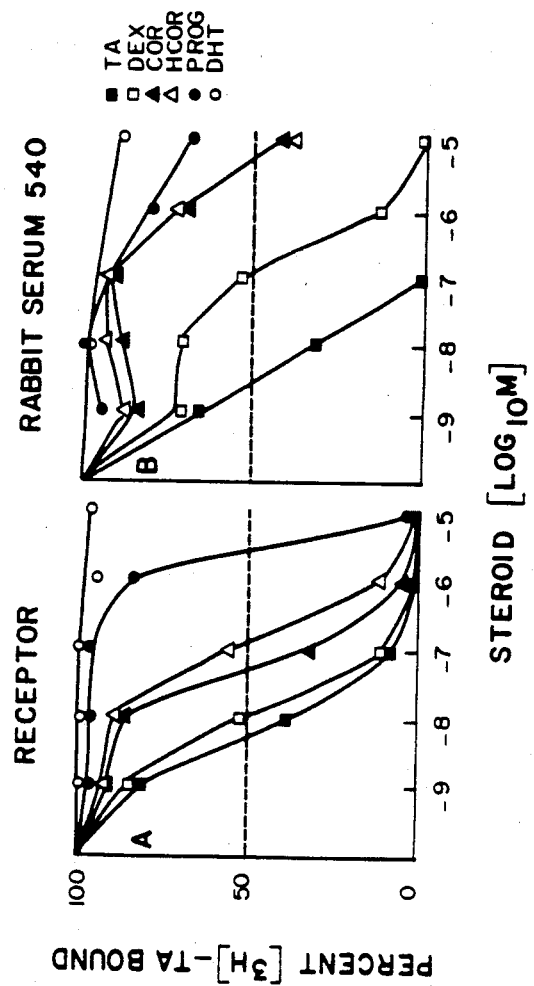
FIG. 4. Competitive inhibition of binding of [$^3$H] triamcinolone to the glucocorticoid receptor and to anti-steroid (unprocessed rabbit serum 540). See legend to Table 1 for the experimental procedure. The inhibitors used were triamcinolone acetonide (■), dexamethason (□), corticosterone (▲), hydrocortisone (Δ), progesterone (●), and dihydrotestosterone (○).

Table I above shows the ligand binding properties of these polyclonal antibodies closely resembled those of the glucocorticoid receptor. Competitive binding studies with [$^3$H] TA as the tracer showed that their pattern of steroid inhibition was similar for the glucocorticoid and the antibody. Triamcinolone was the most potent inhibitor followed in descending order of potency as an inhibitor by dexamethasone, corticosterone, hydrocortisone and progresterone. Dihydrotestosterone had no effect on the binding of [$^3$H]TA to either the glucocorticoid receptor or to the rabbit anti-TA antibody (FIG. 4). The apparent Kd of the anti-steroid in unprocessed rabbit serum for triamcinolone acetonide ($3.2 \times 10^{-9}$ M) was similar to that of The glucocorticoid receptor ($5 \times 10^{-9}$ M) whereas those of the other steriods were about one order of magnitude lower. Although the apparent dissociation constants of the various steroids for the affinity purified antibodies were similar to those of their respective Fab fragments, they were considerably lower than those of the unprocessed serum, indicating that some of the high affinity antibodies were lost during the affinity purification procedure.

As the steroid binding properties of the glucocorticoid receptor and those of the Fab fragments of the affinity purified anti-steriod antibodies were similar, the latter were used to screen by ELISA for anti-idiotypic antibody production in mice.

Isolation of anti-idiotypic antibodies to Fab fragments and the subsets that reacted with the glucocorticoid receptor Auto-anti-idiotypic antibodies to the anti-steriod antibodies were raised by immunizing a mouse with a triamcinolone thyroglobulin conjugate. After the mouse spleen cells were fused with the non-secreting myeloma cell line P3×63-AG8.653, 17 cell lines were found to be produce antibodies that bound to the Fab fragments in ELISA assay. However, only five of these remained positive after the cell lines were expanded.

Antibodies cross reacting with the glucocorticoid receptor were selected from among the anti-idiotypes by their ability to deplete glucocorticoid receptor from rat liver cytosol. The anti-idiotypes were first immobilized on CNBr-Sepharose anti-mouse beads and incubated with rat liver cytosol. After 2 hrs, the beads were centrifuged down and the cytosol labeled with [$^3$H]TA. To account for non-specific binding of the glucocorticoid receptor to the beads controls were included. In these either no anti-idiotype or an anti-idiotype namely 5B5 that did not interact with the anti-steroid by ELISA was immobilized on the beads.

Of all the anti-idiotypic antibodies tested, only 8G11, an IgM was found to bind to the glucocorticoid receptor. As can be seen from Table II below, rat liver cytosol treated with 8G11, immobilized on CNBr-Sepharose antimouse beads would bind 15% less [$^3$H]TA, where a 5B5 would bind only 3% less [$^3$H]TA when compared with cytosol incubated with CNBr-Sepharose antimouse beads containing no anti-idiotype. From Table II, it can also be seen that this depletion was dependent on the amount of rat liver cytosol used in the assay. The amount of glucocoticoid receptor depleted by 8G11-C6 was increased from 15% to 40% by diluting the cytosol containing the glucocorticoid receptor.

TABLE II

| | Cytosol Dil. 2× | | Cytosol Dil. 4× | |
| --- | --- | --- | --- | --- |
| | cpm | % depleted | cpm | % depleted |
| Receptor + BM + 10% FES | 4723 | — | 1682 | — |
| Receptor + 5B5 | 4851 | 3 | 1884 | — |
| Receptor + 8G11 | 3998 | 15 | 1013 | 40 |

Table II: Depletion of glucocorticoid receptor from rat liver cytosol. For the experimental procedure used see methods.

8G11-C6 was subcloned and the monoclones 8G11-G5 and 8G11C6 were derived from this line. These were partially purified by precipitating in 50% (NH$_4$)$_2$SO$_4$. From Table II, it can be seen that CNBR-Sepharose antimouse beads that had no antibody attached to them and treated with BM containing 1% FCS depleted 5% of [$^3$H]TA from rat liver cytosol when compared to anti-mouse beads treated with PBS. Anti-mouse beads with the immobilized control cell line 5B5 or 5B5-B6 also depleted 9% and 4%, respectively, of [$^3$H]TA from rat liver cytosol when compared to the control anti-mouse beads that were treated with PBS. As more [$^3$H]TA receptor was removed from rat liver cytosol by 8G11-C6 than by 8G11-C5 and as the 8G11-C6 cell line resembled the parent cell line 8G11 more closely than 8G11-C5, it was used in all the remaining characterization studies.

Table III shows that prelabeling the receptor by preincubating rat liver cytosol with low levels of [$^3$H]TA (2.5 nM) or high levels [$^3$H]TA (13 nM–50 nM) for 2 hrs at 4° C. and then adding it to CNBr-Sepharose 4B antimouse 8G11-C6 does not inhibit the binding of receptor to the beads. This was again verified by the finding that less cpm (30–65%) were obtained when 8G11-C6 was bound to the beads when compared to 5B5-B6. The epitope recognized by the anti-idiotypic 8G11-C6 therefore might lie near but not in the ligand binding site of the glucocorticoid receptor.

TABLE III

|  | 2 × 5 nM [³H]TA | | 13.0 nM [³H]TA | | 50.0 nM [³H]TA | |
| --- | --- | --- | --- | --- | --- | --- |
|  | cpm | % depleted | cpm | % depleted | cpm | % depleted |
| Receptor + PBS | 1124 |  |  |  |  |  |
| Receptor + 5B5 | 1232 | 0 |  |  |  |  |
| Receptor + 5B5-B6 | 1354 | 0 | 1345 | 0 | 1347 | 0 |
| Receptor + 8G11 | 503 | 61 |  |  |  |  |
| Receptor + 8G11-C6 | 449 | 65 | 934 | 30 | 646 | 52 |

Table III: The effect of prelabeling glucocorticoid receptor with [³H]TA on its removal from rat liver cytosol. The procedure described in the methods section was used, the only difference being that the [³H]TA levels indicated in the Table were used. Also, at high [³H]TA levels (5.0 nM [³H]TA) an additional step was included whereby the supernatant (275 microliters) obtained after the charcoal/dextran step was passed over a dry sephadex G50 column (5 cc capacity) to remove any free [³H]TA.

Figure 5:
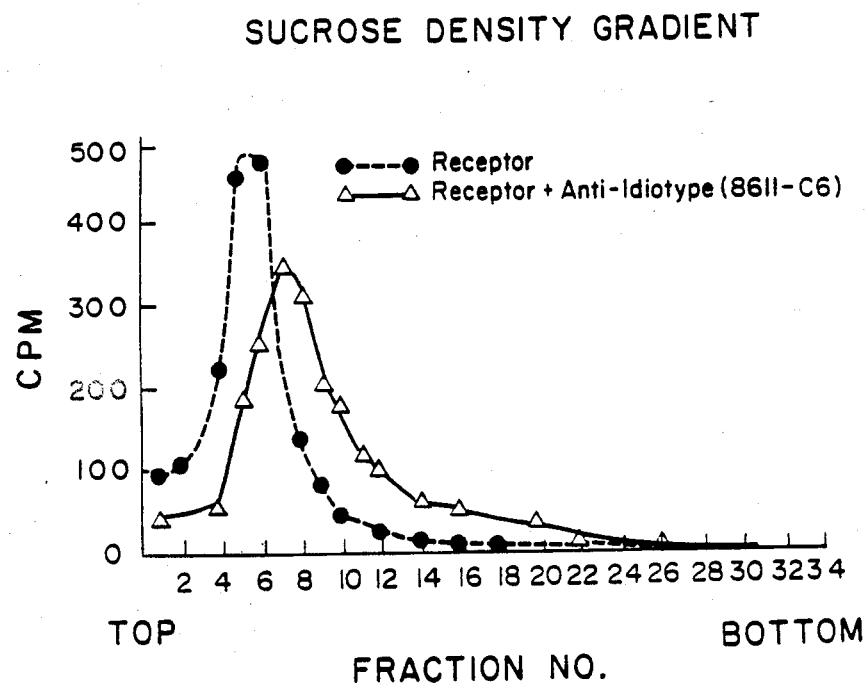
FIG. 5. Sucrose density gradient analysis. Rat liver cytosol (● ●), rat liver cytosol and 8G11-C6 ( Δ Δ ).

More direct evidence of binding of 8G11-C6 to [³H]TA glucocorticoid receptor was obtained from sucrose density studies. As can be seen in FIG. 5 incubation of [³H]TA receptor with 8G11-C6 causes a shift and spread of the elution profile of the glucocorticoid receptor to the right, indicating a protein:protein interaction. However, when assaying by ELISA using goat antimouse IgM to detect the position of 8G11-C6 in the various fractions of the sucrose gradint, IgM was found at the bottom of the tube. From this, it would be expected that the [³H]TA receptor:antibody complex should move to the bottom of the tube if no dissociation of the complex occurs during centrifugation. The present results indicate that 8G11-C6 has a low affinity for the receptor and dissociation of the antibody:receptor complex does occur during centrifugation. The presence of goat antimouse IgM together with 8G11-C6 and receptor shifts the peak of the elution profile again to the left, however, a spread of the elution profile of [³H]TA receptor is still retained.

Characterization of 8G11-C6 by ELISA

1. Specificity of binding of 8G11-C6 to Fab fragments

Figure 6:
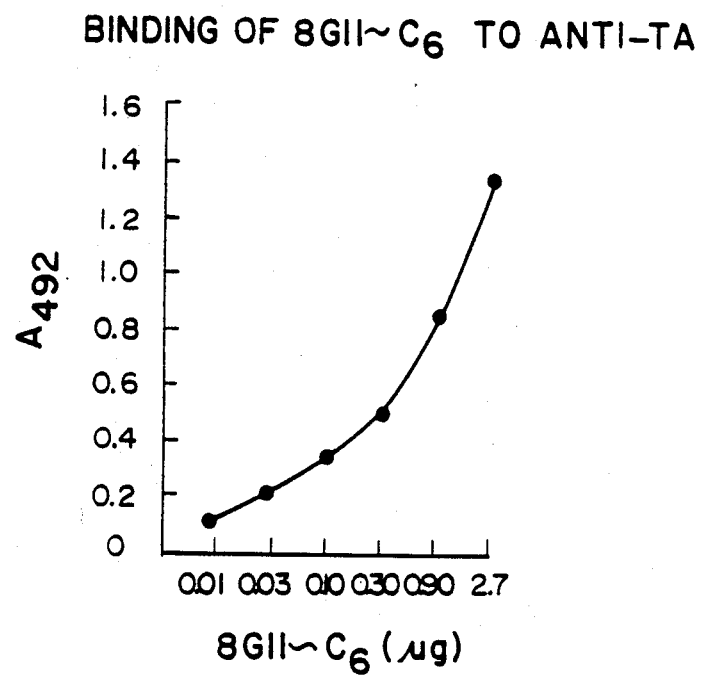
FIG. 6. Binding of 8G11-C6 to anti-steroid Fab fragments. See methods for the experimental procedure. 8G11 C6 was partially purified by precipitating with 50% (NH$_4$)SO$_4$.
Figure 7:
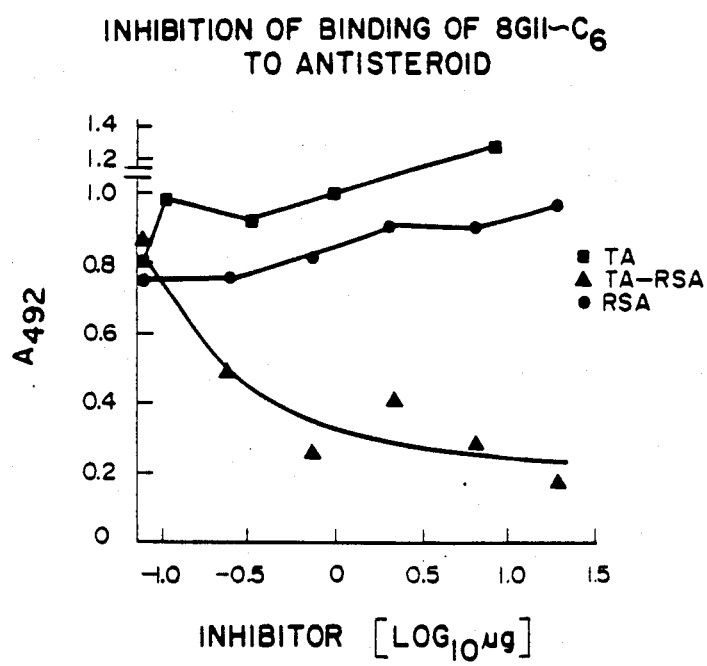
FIGS. 7 and 8. The effect of various steroids, steroid conjugates and RSA on the binding of 8G11-C6 to anti-steroid FAB fragments. The method used was similar to that described in the experimental procedure, the only difference being that 155 microliters of inhibitor that was diluted serially 2-fold with PBS was added to each well and preincubated at room temperature for 10–20 min.
Figure 8:
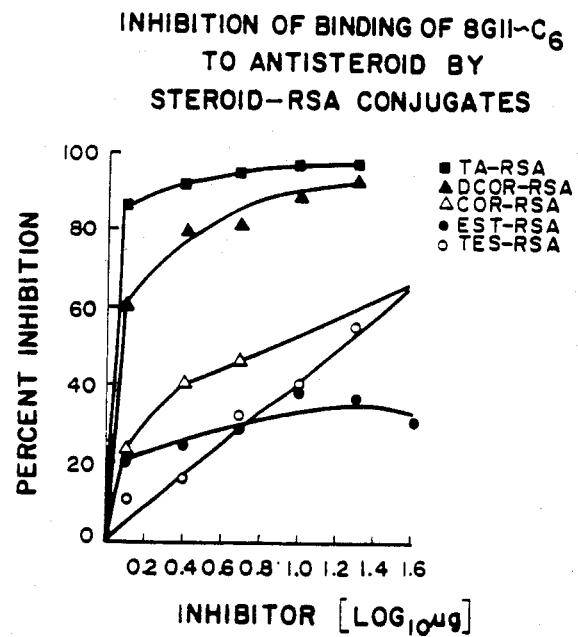

The binding of 8G11-C6 to Fab fragments was found to be concentration dependent (FIG. 6). Although it was found that the ligand, triamcinolone acetonide, or rabbit serum albumin on their own did not affect the binding of 8G11-C6 to Fab, the steroid conjugate i.e. triamcinolone-RSA did inhibit the binding of 8G11-C6 to Fab (FIG. 7). In addition, to triamcinolone-RSA, other steroid-RSA conjugates such as deoxycorticosterone-RSA and cortisone-RSA were also found to inhibit the binding of 8G11-C6 to the anti-steroid Fab fragments. On the other hand, testosterone RSA and estradiol-17β-RSA were found to have only a slight inhibitory effect (FIG. 8). The pattern of inhibition of binding of 8G11-C6 to anti-steroid Fab by the steroid-RSA conjugates resembled that obtained with the competitive binding studies of various steroid with [³H]TA for receptor and anti-steroid antibodies. Neither triamcinolone, nor other steroids such as testosterone and estradiol-17β had any effect on the binding of 8G11-C6 to the anti-steroid Fab fragments. In fact, they appear to produce a slight activation of binding.

The binding of 8G11-C6 to Fab was also inhibited by rat liver cytosol which contain glucocorticoid receptor (FIG. 9). As it could be argued that any other protein or substance in cytosol could cause this inhibition, the glucocorticoid receptor was partially purified from rat liver cytosol. As can be seen from FIG. 9 preparations of partially purified glucocorticoid receptor also inhibited the binding of 8G11-C6 to Fab, having enhanced activity at comparable dilutions.

2. Specificity of binding of 8G11-C6 to partially purified glucocorticoid receptor.

As can be seen from FIG. 10, the binding of 8G11-C6 to plates coated with partially purified glucocorticoid receptor was concentration dependent.

The binding of 8G11-C6 to partially purified receptor was inhibited by triamcinolone-RSA but not by triamcinolone or rabbit serum albumin (FIG. 11). Deoxycorticosterone-RSA also inhibited the binding of 8G11-C6 to partially purified rat liver glucocorticoid receptor. Testosterone had only a slight inhibitory effect whereas estradiol-17β had no effect on this binding. These findings indicate that 8G11-C6 binds to a protein in the partially purified preparations that interacts with the steroid conjugate.

REFERENCES

1. Eisen, H. J. Proc. Natl. Acad. Sci. USA 77:3893–3897 (1980)
2. Govindan, M. and Sekeris, C. E. Europ. J. Biochem. 89:95–104 (1978).
3. Tswadaroglore, N. G., Govindan, M. V., Schmid, W. and Sekeris, C. E. Europ. J. Biochem. 114:305–313 (1981).
4. Okret, S., Carlstedt-Duke, J. Wrange, O. Carlstrom, K. and Gustafsson, J-A. Biochem. Biophys. Acta 677:205–219 (1981).
5. Bernard, P. A. and Joh, T. H. Arch. Biochem. Biophys. 229:466–476 (1984).
6. Westphal, H. M., Moldenhauer, G. and Beato, M. EMBO. 1:1467–1471 (1982).
7. Grandics, P., Gasser, D. L. and Litwack, G. Endocr. III:1731–1733 (1982).
8. Okret, S., Wikstro, A-C., Wrange, O, Anderson, G. and Gustafsson, J-A. Proc. Natl. Acad. Sci. USA 81:1609–1613 (1984).
9. Gametchu, B. and Harrison, R. W. Endocrinol 114:274–279 (1984).
10. Wassermann, N. H., Penn, A. S., Freimuth, P., Wentzel, S., Cleveland, W. L. and Erlanger B. F. Proc. Natl. Acad. Sci. USA 79:4810–4814 (1982).
11. Cleveland, W. L., Wasserman, N. H., Sarangarajan, R., Penn, A.S. and Erlanger, B.F. Nature 305:56–57 (1983).
12. Sege, K. and Peterson, P. A. Proc. Natl. Acad. Sci. USA 75:2443–2447 (1978).
13. Schreiber, A. B., Couraud, P. O., Andre, C., Vray, B. and Strosberg, A. D. Proc. Natl. Acad. Sci. USA 77:7385–7389 (1980).
14. Homcy, C. J., Rockson, S. G. and Haber, E. J. Clin. Invest. 69:1147–1153 (1982).
15. Marasco, W. A. and Becker, E. L. J. Immunol. 128:963–968 (1982).
16. Farid, N. R. Pepper, B., Urbina-Briones, R. and Islam, N. R. J. Cell. Biochem. 19:305–313 (1982).
17. Nepom, J. T., Weiner, H. L., Dichter, M. A. et al. J. Exp. Med. 155–163 (1982).
18. Schreiber, M., Fogelfield, L. F., Souroujon, M. C., Kohn, F. and Fuchs, S. Life Sci. 1519–1529 (1983).
19. Randerath, K. General Behavior on thin-layer chromotograms p. 203, Verlag Chemie, Academic Press (1963).
20. Erlanger, B. F., Borek, F., Beiser, S. M. and Lieberman, S., J. Biol. Chem. 713–727 (1957).

21. Erlanger, B. F., Borek, F., Beiser, S. M. and Lieberman, S., J. Biol. Chem. 1090–1094 (1959).
22. Porter, Biochem. J. 73:119 (1959).
23. Kewney, J. F., Radbruch, B. L. and Rajewsky, K. J. Immunol. 123:1548–1550 (1979).
24. Kohler, G. and Milstein, C. Nature 256:495–497 (1975).
25. Sharon, J., Morrison, S. L. and Kabat, E. A. Proc. Natl. Sci. USA 76:1420–1424 (1979).
26. Cleveland, W. L. and Erlanger, B. F. manuscript in preparation.
27. Oudin, U. and Michael, M. Cr. Hebd. Seanc. Acad. Sci., Paris 257:805–808 (1963).
28. Kunkel, H. G., Mannick, M. and Williams, W. C. Science 140:1218–1219 (1963).
29. Jerne, N. L. Anals. Inst. Pasteur, Paris 125C:373–339 (1974).
30. Schechter, Y., Maron, R., Elias, D. & Cohen, I.R., Science 216:542–544 (1982).
31. Jensen E. V. & Green, G. L., Dev. Endocrinol 317–333 (1981).
32. Yavin, E., Horiz, Biochem. Biophys., 6(Hormone Receptors) 67–81 (1982).
33. Waldor, M. K. et al., Natn. Acad. Sci. U.S.A. 80:2713–2717 (1983).
34. Bartels, E., Wassermann, N. H. & Erlanger, B. F., Proc. Natn. Acad. Sci. U.S.A. 68:1820–1823 (1971).
35. Wassermann, N. H., Bartels, E. & Erlanger, B. F., Proc. Natn. Acad. Sci. U.S.A. 76:256–259 (1979).
36. Heidmann, T. & Changeux, J. P., A. Rev. Biochem. 47:317–357 (1978).
37. Geha, R. S., J. Immun. 129:139–144 (1982).

What is claimed is:

1. Hybridoma 8G11C6 (ATCC No. HB 8708).

2. Anti-idiotypic monoclonal antibody produced by the hydridoma of claim 1.

3. A qualitative competitive immunoassy for detecting a glucocorticoid receptor which comprises:
   (a) contacting material suspected of containing the glucocorticoid-receptor with the anti-idiotypic monclonal antibody of claim 2 so as to form a complex which includes the anti-idiotypic monoclonal antibody and the glucocorticoid-receptor; and
   (b) detecting the presence of the complex and thereby the presence of the glucocorticoid-receptor.

4. A qualitative histochemical assay for detecting in a biological sample the presence of a glucocorticoid-receptor in either inactive or activated form, wherein the activated form results upon addition of a glucocorticoid to the biological sample which comprises:
   (a) for the inactive form, incubating the biological sample with the anti-idiotypic monoclonal antibody of claim 2 so as to form a complex which includes the anti-idiotypic monoclonal antibody and the glucocorticoid-receptor, or for the inactivated form, incubating the biological sample with the glucocorticoid so as to bind the glucocorticoid-receptor and form a glucocorticoid, glucocorticoid-receptor complex, and then contacting the resulting complex with the anti-idiotypic monoclonal antobody of claim 2 so as to form a complex which includes glucocorticoid, the glucocorticoid-receptor, and the anti-idiotypic monoclonal antibody;
   (b) removing anti-idiotypic monoclonal antibody which is not part of the complex from the sample;
   (c) contacting the resulting sample with a detectably labeled antibody or a detectably labeled antibody fragment capable of binding to the anti-idiotypic monoclonal antibody under conditions permitting the labeled antibody or antibody fragment to bind to the anti-idiotypic monoclonal antibody; and
   (d) determining the presence of detectably labeled antibody or detectably labeled antibody fragment bound to the monoclonal antibody, and thereby the presence of glucocorticoid-receptor in the sample.

5. A method of claim 4, wherein the glucocorticoid is triamcinolone.

6. A quantitative histochemical assay for determining in a biological sample the amount of a glucocorticoid-receptor in either inactive or activated form, wherein the activated form results upon addition of a glucocorticoid to the biological sample which comprises:
   (a) (i) for the inactive form, incubating the biological sample with a predetermined amount of the anti-idiotypic monoclonal antibody of claim 2 so as to form a complex which includes the anti-idiotypic monoclonal antibody and the glucocorticoid-receptor, or (ii) for the activated form, incubating the biological sample with a predetermined amount of glucocorticoid so as to bind the glucocorticoid-receptor and form a glucocorticoid, glucocorticoid-receptor complex, and then contacting the resulting complex with the anti-idiotypic monoclonal antibody of claim 2 so as to form a complex which includes glucocorticoid, the glucocorticoid-receptor, and the anti-idiotypic monoclonal antibody;
   (b) removing anti-idiotypic monoclonal antibody which is not part of the complex from the sample;
   (c) contacting the resulting sample with a detectably labeled antibody or a detectably labeled antibody fragment capable of binding to the anti-idiotypic monoclonal antibody under conditions permitting the labeled antibody or antibody fragment to bind to the anti-idiotypic monoclonal antibody; and
   (d) determining the amount of detectably labeled antibody or detectably labeled antibody fragment bound to the anti-idiotypic monoclonal antibody, and thereby the amount of glucocorticoid-receptor in the sample.

7. A method of claim 6, wherein the glucocorticoid is triamcinolone.

8. A method for obtaining purified glucocorticoid-receptor which comprises:
   (a) immobilizing the anti-idiotypic monoclonal antibody of claim 2 on a support;
   (b) contacting the immobilized anti-idiotypic monoclonal antibody with material containing glucocorticoid-receptor under conditions permitting the glucocorticoid-receptor to bind to the anti-idiotypic monoclonal antibody;
   (c) separating unbound material from the immobolized anti-idiotypic monoclonal antibody to which the glucocorticoid-receptor is bound; and
   (d) treating the bound receptor so as to elute the glucocorticoid-receptor from the immobilzed anti-idiotypic monoclonal antibody; and
   (e) recovering purified glucocorticoid-receptor.

9. A method of claim 8, wherein the glucocorticoid-receptor is a receptor for triamcinolone.

10. The anti-idiotypic monoclonal antibody of claim 2, detectably labeled.

11. The detectably labeled, anti-idiotypic monoclonal antibody of claim 10, wherein the detectable label comprises a fluorescent moiety bound to the antibody.

12. The detectably labeled, anti-idiotypic monoclonal antibody of claim 10, wherein the detectable label comprises an enzyme bound to the antibody.

13. A quantitative immunoassay for determining the amount of glucocorticoid receptor which comprises:
   (a) contacting material containing the glucocorticoid-receptor with the anti-idiotypic monoclonal antibody of claim 2 so as to form a complex which includes the anti-idiotypic monoclonal antibody and the glucocorticoid-receptor;
   (b) determining the amount of complex so formed; and
   (c) relating the amount of complex so formed to the amount of glucocorticoid receptor present in the material.

14. A method of claim 13, wherein the anti-glucocorticoid antibody or fragment of anti-glucocorticoid antibody is immobilized on a support and the material not bound to the immobilized antibody or fragment is removed prior to determining the amount of complex formed.

15. A method of claim 13, wherein the material is a tissue extract.

16. A method for producing a anti-idiotypic monoclonal antibody capable of binding to glucocorticoid-receptor which comprises:
   (a) contacting lymphoid cells from an animal with an effective antibody-raising amount of an antigen comprising a triamcinolone derivative;
   (b) collecting the lymphoid cells a period of time after contacting the cells with the antigen;
   (c) fusing the collected lymphoid cells with appropriate myeloma cells to produce hybridoma cells each of which produces a monoclonal antibody;
   (d) screening the hybridoma cells so produced to identify a hybridoma cell which produces a monoclonal antibody capable of binding to the glucocorticoid-receptor;
   (e) separately cultivating the hybridoma cell so identified on a medium; and
   (f) separately recovering the anti-idiotypic monoclonal antibody produced by the hybridoma cell.

17. A method of claim 16, wherein the triamcinolone is derivatized to δ-ketohexanoic hydroxysuccinimide ester at the 16 and 17 position of the D ring of the triamcinolone.

* * * * *